(12) United States Patent
Holliday et al.

(10) Patent No.: US 7,594,288 B1
(45) Date of Patent: Sep. 29, 2009

(54) PILLOW HAVING ANTI-SNORING PROPERTIES

(75) Inventors: James Mike Holliday, Hickory, NC (US); Bradley Coleman McNeely, Hickory, NC (US); James Alexander Wall, Hickory, NC (US); Gerry Borreggine, Hickory, NC (US)

(73) Assignee: I Care Sleep, LLC, Raleigh, NC (US)

( * ) Notice: Subject to any disclaimer, the term of this patent is extended or adjusted under 35 U.S.C. 154(b) by 0 days.

(21) Appl. No.: 11/904,795

(22) Filed: Sep. 28, 2007

(51) Int. Cl.
*A47C 20/00* (2006.01)

(52) U.S. Cl. .................................... 5/636; 5/640; 5/630

(58) Field of Classification Search .............. 5/630, 5/636–637, 640
See application file for complete search history.

(56) References Cited

U.S. PATENT DOCUMENTS

| | | | |
|---|---|---|---|
| 2,167,622 A | 8/1939 | Bentivoglio | 5/338 |
| 2,898,975 A | 8/1959 | Wagner | 155/179 |
| 4,118,813 A | 10/1978 | Armstrong | 5/337 |
| 4,748,702 A | 6/1988 | Sandler | 5/434 |
| 4,832,007 A * | 5/1989 | Davis et al. | 250/580 |
| 4,850,067 A | 7/1989 | Latorre | 5/431 |
| 4,908,893 A | 3/1990 | Smit | 5/434 |
| 5,016,303 A | 5/1991 | Tanaka et al. | 5/437 |
| 5,054,143 A | 10/1991 | Javaher | 5/434 |
| 5,781,947 A | 7/1998 | Sramek | 5/636 |
| 5,848,448 A | 12/1998 | Boyd | 5/636 |
| 5,920,932 A | 7/1999 | Hershgordon | 5/636 |
| 5,926,880 A | 7/1999 | Sramek | 5/636 |
| 6,006,380 A | 12/1999 | Sramek | 5/636 |
| 6,513,179 B1 | 2/2003 | Pan | 5/636 |
| 6,574,809 B1 | 6/2003 | Rathbun | 5/636 |
| 6,671,907 B1 | 1/2004 | Zuberi | 5/636 |
| 6,915,539 B2 | 7/2005 | Rathbun | 5/636 |
| 7,020,919 B2 | 4/2006 | Inaba | 5/638 |
| 7,082,633 B1 | 8/2006 | Maarbjerg | 5/636 |
| 7,100,227 B2 | 9/2006 | Frisbee | 5/640 |
| 7,127,759 B2 | 10/2006 | Koops | 5/644 |
| 7,203,983 B1 | 4/2007 | Reeves et al. | 5/636 |
| 7,213,280 B2 | 5/2007 | Lavin et al. | 5/636 |
| 7,216,387 B2 | 5/2007 | Laxton | 5/636 |
| 7,316,041 B2 * | 1/2008 | Guez | 5/636 |
| 2004/0139548 A1 | 7/2004 | Hwang-Pao | 5/636 |
| 2006/0260055 A1 | 11/2006 | Frisbee | 5/636 |
| 2006/0265808 A1 | 11/2006 | Phillips | 5/637 |
| 2007/0011812 A1 | 1/2007 | Drucker | 5/636 |

* cited by examiner

*Primary Examiner*—Fredrick Conley
(74) *Attorney, Agent, or Firm*—K&L Gates LLP

(57) ABSTRACT

A pillow for supporting the head of a user during sleeping, having a generally rectangular main body of resiliently compressible foam material presenting a lower surface configured to overlie stably on a sleeping platform and an upper surface for supporting a user's head. An interior void extending longitudinally between opposite ends of the main body generally centrally between the upper and lower surfaces and generally centrally between the longitudinal sides of the main body. A central opening extends interiorly into the main body and merges into the interior void of the main body. The upper surface generally surrounding the central opening defines a central head support area and the upper surface generally between the central opening and an adjacent longitudinal side of the main body defines a neck support area which, in cooperation with the central opening and the interior void, supports a user's head and neck when in an upwardly facing disposition with the head tilted slightly relative to the neck to tend to open breathing passages through the user's nose and throat to mitigate snoring.

5 Claims, 4 Drawing Sheets

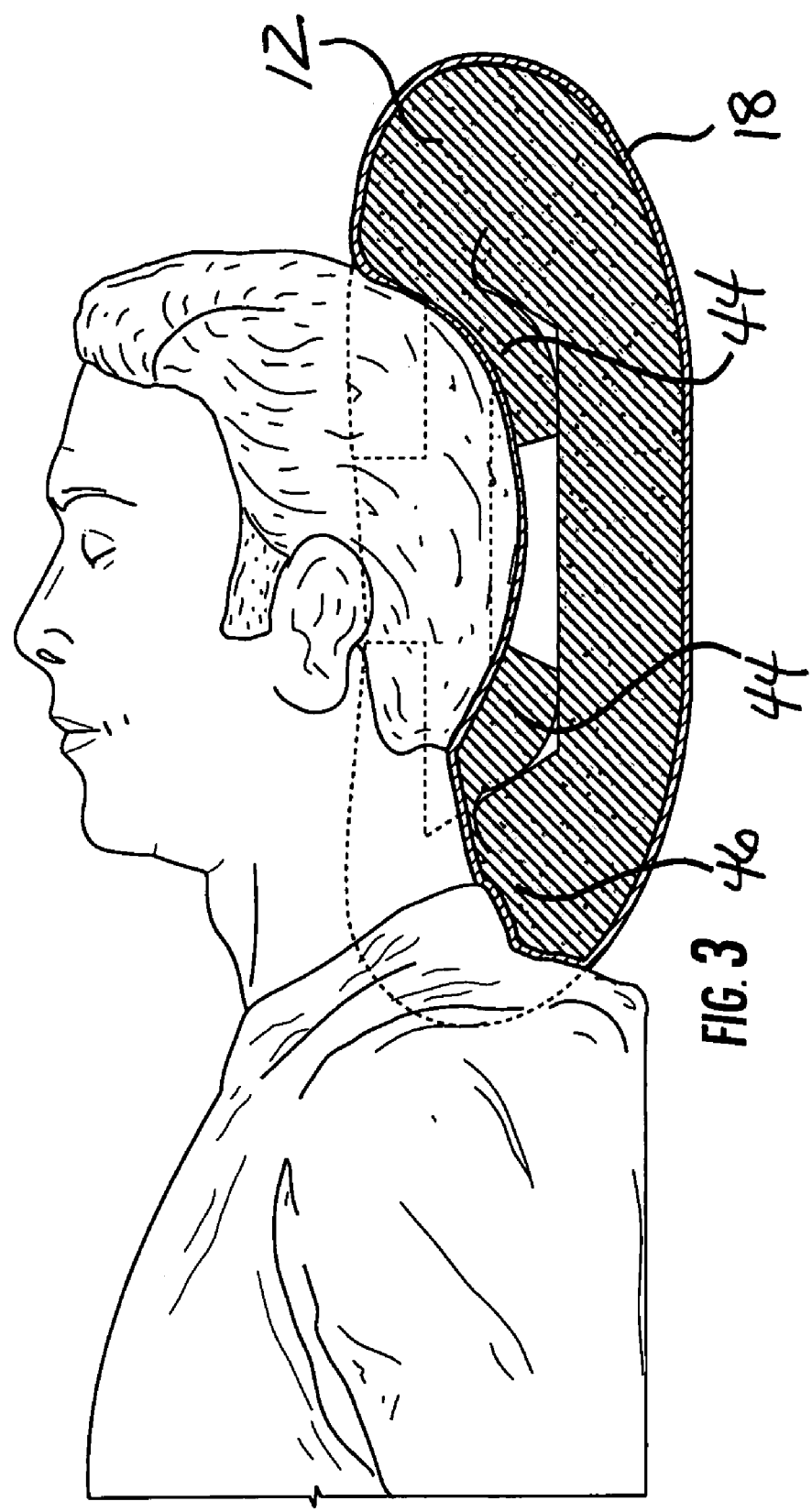

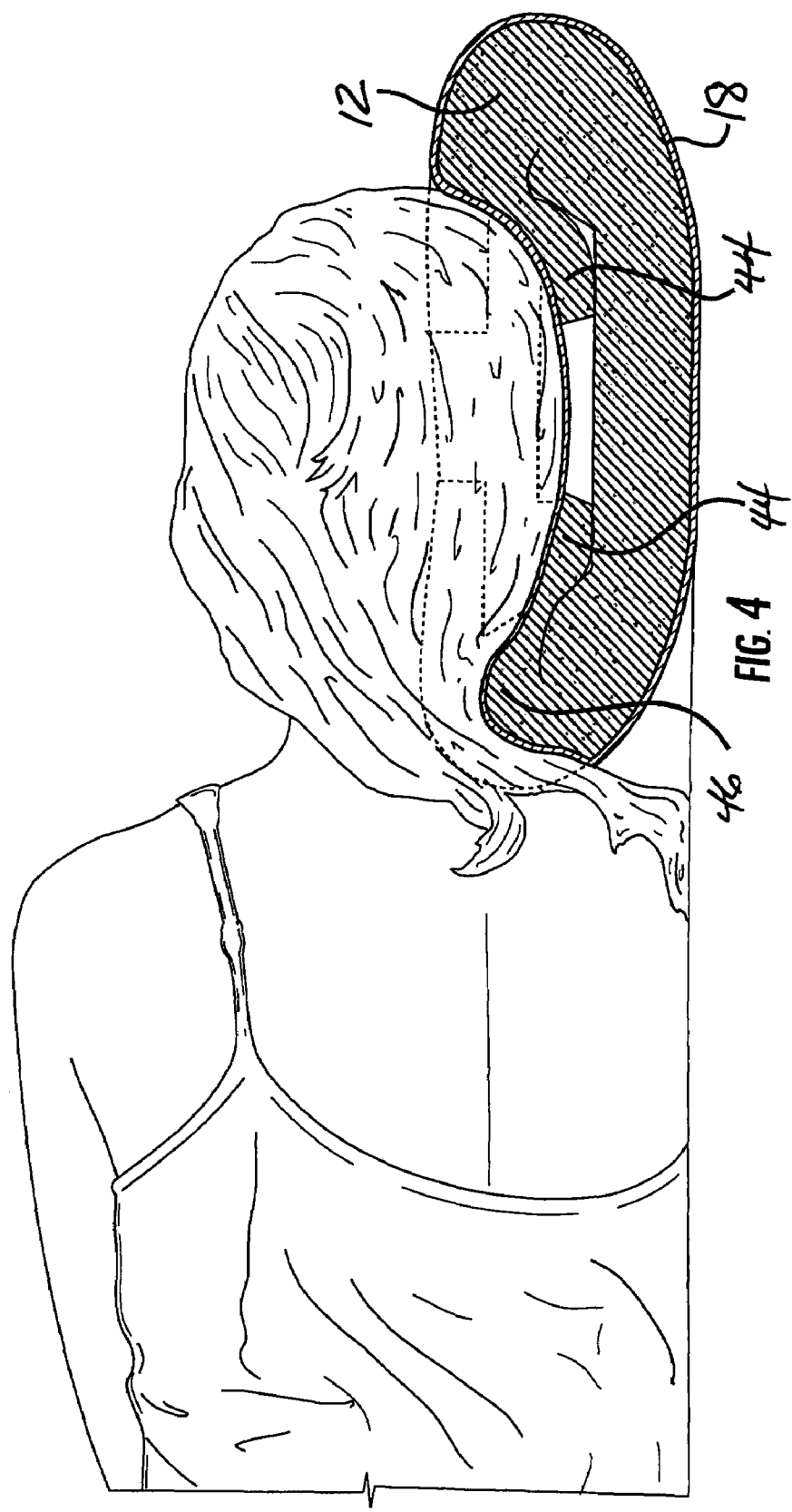

PILLOW HAVING ANTI-SNORING PROPERTIES

BACKGROUND OF THE INVENTION

The present invention relates generally to pillows adapted for use in supporting a user's head during sleeping and, more particularly, to sleeping pillows having a capability for deterring or mitigating snoring by a user during sleeping.

For many years, pillows used for sleeping have remained largely unchanged, typically being made of a rectangular textile covering stuffed with natural feathers, a comparable synthetic material, or a rectangular block of a compressible form. Over recent years, by contrast, a considerably greater amount of technological effort has been devoted to the design of specialized materials and configurations for pillows for various purposes ranging from improving comfort to prevention of snoring to the mitigation of facial wrinkling during sleeping. The diversity of pillow constructions known in the state of the art is representatively illustrated by U.S. Pat. Nos. 2,167,622; 2,898,975; 4,118,813; 4,748,702; 4,850,067; 4,908,893; 5,016,303; 5,054,143; 5,781,947; 5,848,448; 5,920,932; 5,926,880; 6,006,380; 6,513,179; 6,574,809; 6,671,907; 6,915,539; 7,020,919; 7,082,633; 7,100,227; 7,127,759; 7,203,983; 7,213,280; and 7,216,387; and by published U.S. Patent Applications Nos. 2004/0139548; 2006/0260055; 2006/0265808; 2007/0011812.

Of these patents and applications, U.S. Pat. Nos. 4,748,702; 4,850,067; 5,920,932; 7,100,227; and 7,127,759; and published U.S. Patent Applications Nos. 2006/0260055 and 2007/0011812, are specifically concerned with the prevention or deterrence of snoring by a user during sleeping.

It is not believed that any of the anti-snoring pillows proposed in the above-identified patents have ever met with any significant degree of commercial success, yet the attention to this problem evidenced by the developmental efforts devoted to these pillow constructions indicates the existence of a recognized desire and need among consumers for a pillow which will effectively mitigate snoring during sleeping.

SUMMARY OF THE INVENTION

It is accordingly an object of the present invention to provide an improved head support pillow which will deter or mitigate a user's tendency to snore while sleeping.

Briefly summarized, the present invention contemplates the formation of such a pillow to comprise a main body formed of a resiliently compressible foam material in a generally rectangular configuration having opposite ends, opposite longitudinal sides, and opposed upper and lower surfaces extending between the opposite ends and opposite sides, with the lower surface being configured to lie stably on a sleeping platform. According to the present invention, the main body is formed with an interior void extending longitudinally between the opposite ends of the main body generally centrally between the upper and lower surfaces and generally centrally between the longitudinal sides of the main body, and the upper surface is formed with a generally central opening extending interiorly into the main body and merging into the interior void of the main body. Thus, the upper surface generally surrounding the central opening defines a central head support area and the upper surface generally between the central opening and an adjacent longitudinal side of the main body defines a neck support area. The head and neck support areas, in cooperation with the central opening and the interior void, are adapted to support a user's head and neck, when in an upwardly facing disposition, with the head tilted slightly relative to the neck so as to tend to open breathing passages through the user's nose and throat, and to support the user's head, neck and spine, when in a laterally side-facing disposition, in a natural alignment with one another, so as to mitigate a tendency of the user to snore.

In a preferred embodiment of the pillow of the present invention, the upper surface further comprises facial support areas between the central opening and each opposite end of the main body adapted to support a side of a user's face. Preferably, the interior void inwardly adjacent the facial support areas promotes reduction of pressure on a user's ear when a side of the user's face is supported on one of the facial support areas. The main body of the pillow may advantageously be made of a visco-elastic foam material. The pillow may further comprise a cover generally enclosing the main body.

A preferred embodiment of the pillow may be constructed with the main body having a primary body component defining the generally rectangular configuration of the main body and formed longitudinally through a central interior area thereof with an elongated channel of a generally trapezoidal cross-sectional shape and with a constricted elongated slot opening outwardly from the trapezoidal channel along substantially the length thereof. Separate insert body components are secured in spaced relation to each other within opposite ends of the slot and within the trapezoidal channel such that the primary and insert body components define the interior void and the central opening of the main body.

BRIEF DESCRIPTION OF THE DRAWINGS

FIG. 3 is a vertical cross-sectional view through the sleeping pillow of FIGS. 1 and 2, depicting the pillow in use by a user; and FIG. 4 is another vertical cross-sectional view, similar to FIG. 3, also depicting the sleeping pillow of FIGS. 1 and 2 in use by a user, situated in a different sleeping orientation.

DETAILED DESCRIPTION OF THE PREFERRED EMBODIMENTS

Figure 1:
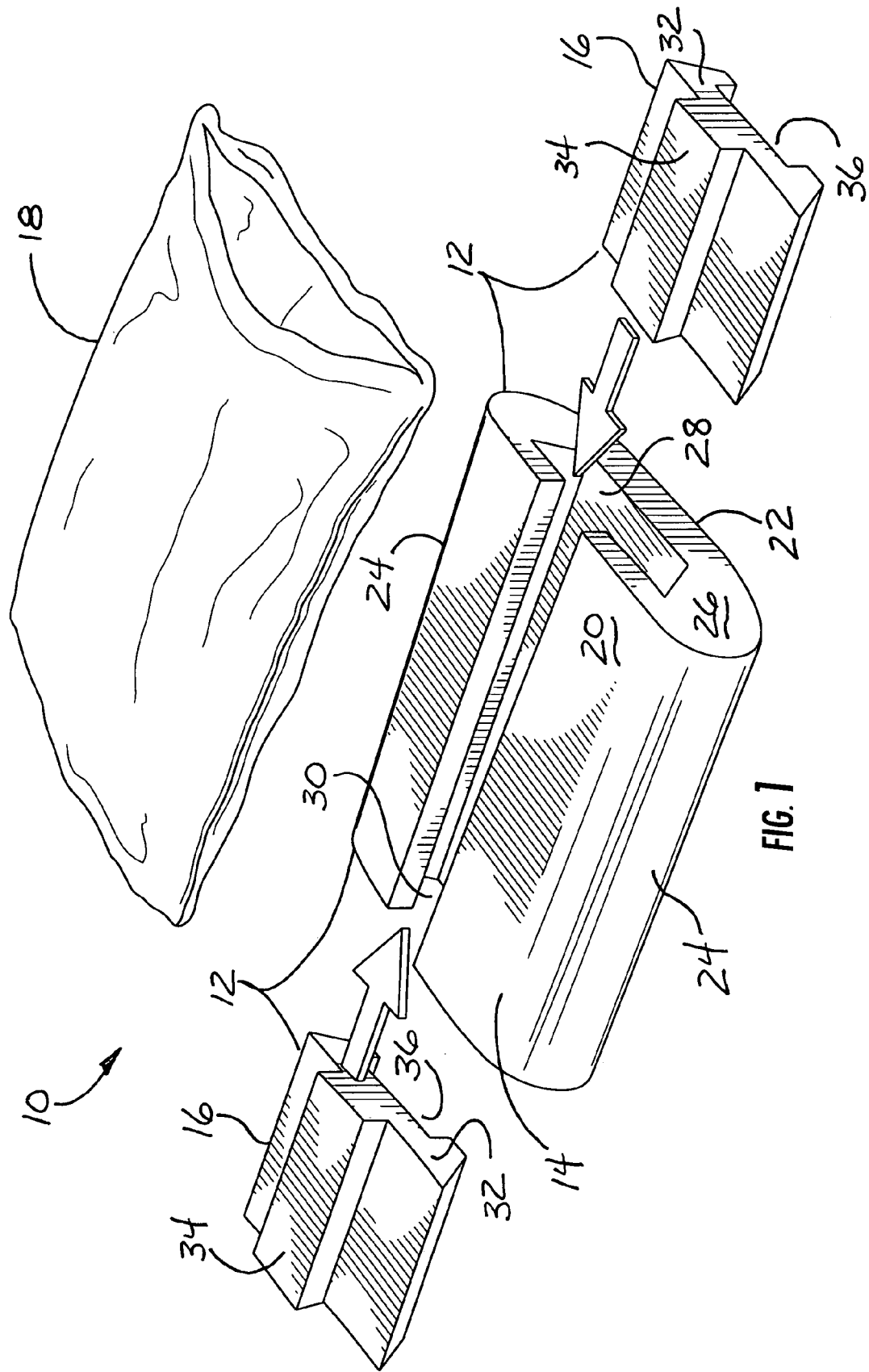
FIG. 1 is an exploded perspective view of a sleeping pillow according to a preferred embodiment of the present invention.
Figure 2:
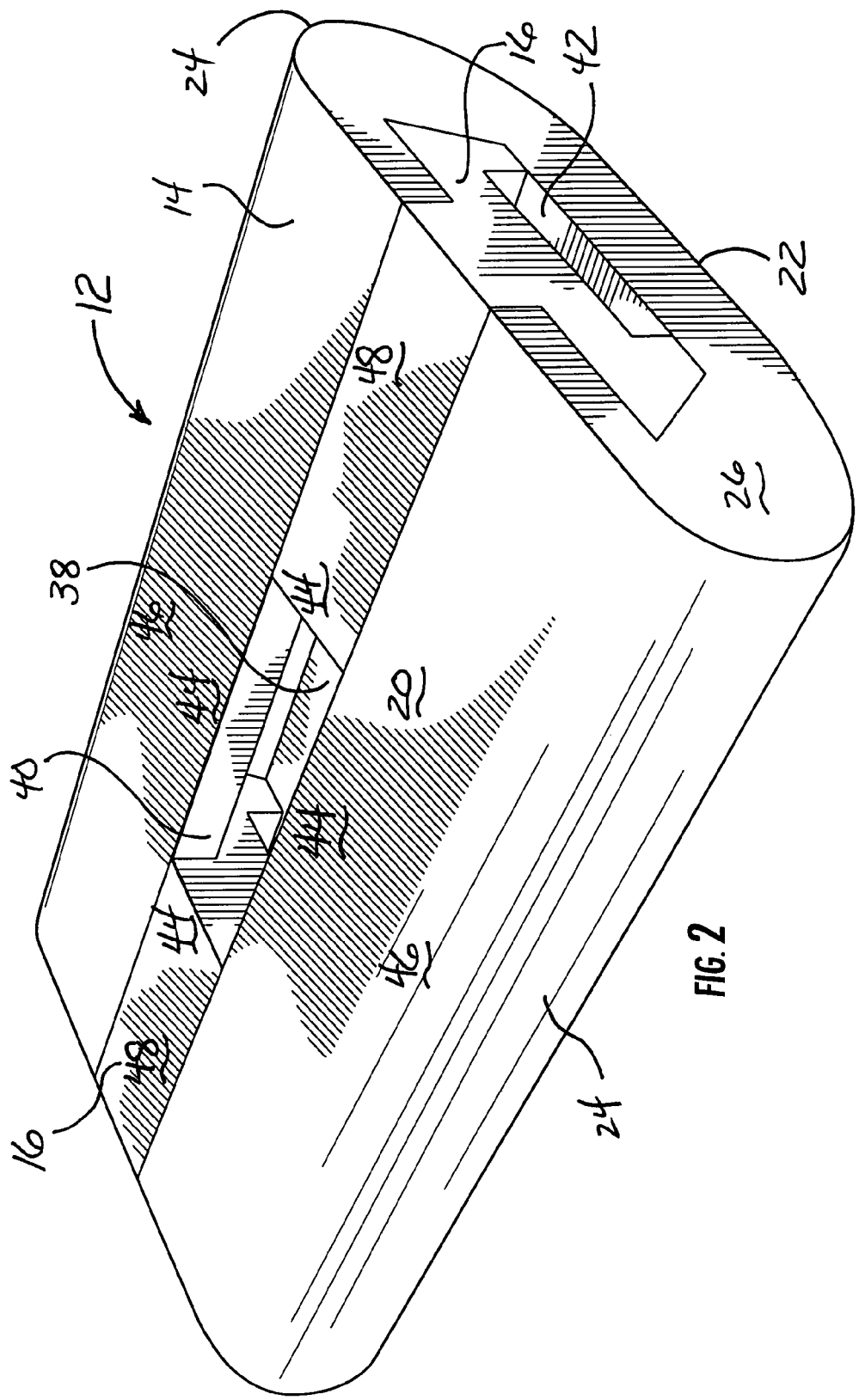
FIG. 2 is a perspective view, similar to FIG. 1, depicting the body of the sleeping pillow in assembled condition, but omitting the pillow cover.

Referring now to the accompanying drawings and initially to FIG. 1, a pillow in accordance with the present invention is depicted in three-dimensional perspective view with its constituent components exploded for clarity, the pillow in its totality being indicated by the referenced numeral 10. The pillow 10 basically comprises a main body 12 formed of a primary body component 14 and a pair of insert body components 16 adhesively bonded with the primary body component 14, all of which is encased within a surrounding textile covering 18.

The main body 12 of the pillow 10 is preferably formed of a resiliently compressible foam material, which may be of any various known types of polymeric foam including, by way of example but without limitation, polyurethane foam, synthetic so-called foam rubber, latex foam, or visco-elastic foam (commonly referred to as "memory foam"). A visco-elastic "memory" foam material is preferred for its ability to mold and conform to the shape of an object lying thereon and to spread uniformly the force of pressure exerted by the object.

The main body 12 is preferably cut from a single homogenous unitary block of the selected foam material into an essentially rectangular overall configuration with generally flat upper and lower surfaces 20, 22 rounded at the opposite lengthwise sides 24 but cut substantially flat in essentially perpendicular relation to the upper and lower surfaces 22, 24 at the opposite lengthwise ends 26 of the body 12. The foam block is cut lengthwise in the upper surface 20 and into the central interior area of the foam block to remove a section of the foam material along the entire length of the main body 12 between its opposites ends 26, thereby forming the primary body component 14 with an elongated interior channel 28 of a generally trapezoidal cross-sectional shape and with a constricted elongated slot 30 opening outwardly from the trapezoidal channel 28 to the upper surface 20, each extending the entire length of the primary body component 14. The removed section of the foam block is then cut laterally to form the two insert body components 16 of a shortened collective length less than the full length of the primary body component 14, with each insert body component 16 having a main trapezoidal body portion 32 with a narrow rectangular body portion 34 centrally along one side of the trapezoidal body portion 32. The opposite side of the trapezoidal body portion 32 is further cut to remove a rectangular channel section 36 therefrom. The cutting of the foam block to thusly form the primary and insert body components 14, 16 may advantageously be performed utilizing any known form of computer numerically controlled (CNC) cutting machine.

The primary and insert body components 14, 16 are then reassembled by adhesively gluing the insert body components 16 in spaced relation to one another within the opposites ends of the void in the primary body component 14 formed by the trapezoidal channel 28 and the slot 30. In this manner, the spacing between the two insert body components 16 defines a central opening within the main body 12 configured as a substantially trapezoidal void 38 within the main body generally centrally between its upper and lower surfaces 20, 22 and generally centrally between its longitudinal sides 24, which opens upwardly to the upper surface 20 through the more narrow portion 40 of the slot 30 between the insert body components 16. The respective channel sections 36 of the insert body components 16 are aligned with one another and open into the central trapezoidal void 38 to form an uninterrupted void 42 extending the full length of the main body between its opposite ends 26 centrally between the upper and lower surfaces 20, 22 and centrally between the longitudinal sides 24 of the main body 12.

The upper surface 20 of the main body 12 formed by the assembled primary and insert body components 14, 16 surrounding the central slotted opening 40 define support areas 44 for a user's head while the portions of the upper surface 20 generally between the central slotted opening 40 and the adjacent longitudinal sides 24 of the main body 12 define support areas 46 for a user's neck. In this manner, as depicted in FIG. 3 of the drawings, when a user's head is rested on the upper surface 20 of the pillow at the location of the central slotted opening 40 and with the user's face oriented upwardly, the head and neck support areas 44, 46 in cooperation with the open areas 38, 40, 42, support the user's head at a slightly tilted orientation relative to the neck thereby tending to fully open the breathing passageways through the user's nose and throat. Alternatively, with a user's head resting centrally on the upper surface 20 of the pillow 10 in a laterally side-facing disposition or orientation, as depicted in FIG. 4, the head and neck support areas 44, 46 in conjunction with the open areas 38, 40, 42 support the user's head, neck and spine in a natural alignment. In each orientation of a user's head, the potential tendency of a user to snore as a result of constricted breathing passageways or a misalignment of the head, neck and spine is mitigated.

The upper surface 20 of the main body 12 adjacent each opposite end 26 thereof further form facial support areas 48 generally over the respective insert body components 16, on which a user's head may also be rested in either an upwardly facing or laterally side-facing disposition. With a user's head rested on one of the facial support areas 48 in a side-facing disposition, the side of the user's face and head are supported while the lengthwise interior void 42 formed by the removed channel section 36 of the respective interior body components 16 promotes a reduction of pressure on the user's ear to further enhance a user's comfort when sleeping on the pillow 10.

The textile case 18 enclosing the assembly of the main body 12 is preferably fashioned into the form of an enclosed envelope closely fitted in surrounding relationship thereto. The case 18 may be fashioned from substantially any form of suitable textile material, including woven and knitted fabric of natural and synthetic fibers or filaments. A particularly advantageous form of textile case 18 is made from "Cuprotex" textile fabrics made of copper-infused "Cupron" yarns marketed by Cuprotex, LLC, Greensboro, N.C. Such a textile case 28 provides anti-microbial (anti-fungal and anti-bacteria) properties, and is allergen and odor free.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

What is claimed is:

1. A pillow for supporting the head of a user during sleeping, the pillow comprising:

a main body formed of a resiliently compressible foam material in a generally rectangular configuration having opposite ends, opposite longitudinal sides, and opposed upper and lower surfaces extending between the opposite ends and opposite sides, the lower surface being configured to lie stably on a sleeping platform, the main body being formed with an interior void extending longitudinally between the opposite ends of the main body generally centrally between the upper and lower surfaces and generally centrally between the longitudinal sides of the main body, and the upper surface being formed with a generally central opening extending interiorly into the main body and merging into the interior void of the main body, the upper surface generally surrounding the central opening defining a central head support area and the upper surface generally between the central opening and an adjacent longitudinal side of the main body defining a neck support area which, in cooperation with the central opening and the interior void, are adapted to support a user's head and neck, when in an upwardly facing disposition, with the head tilted slightly relative to the neck so as to tend to open breathing passages through the user's nose and throat, and to support the user's head, neck and spine, when in a laterally side-facing disposition, in a natural alignment, so as to mitigate a tendency to snore, wherein the main body includes a primary body component defining the generally rectangular configuration of the main body and formed longitudinally through a central interior area thereof with an elongated channel of a generally trapezoidal cross-sectional shape and with a constricted elongated slot opening outwardly from the trapezoidal channel along substantially the length thereof, and insert body components secured in spaced relation to each other within opposite ends of the slot and within the trapezoidal channel, the primary and insert body components defining the interior void and the central opening of the main body.

2. A pillow for supporting the head of a user during sleeping according to claim 1, the upper surface further comprises facial support areas between the central opening and each opposite end of the main body adapted to support a side of a user's face.

3. A pillow for supporting the head of a user during sleeping according to claim 2, wherein the interior void inwardly adjacent the facial support areas promotes reduction of pressure on a user's ear when a side of the user's face is supported on one of the facial support areas.

4. A pillow for supporting the head of a user during sleeping according to claim 1, wherein the main body comprises a visco-elastic foam material.

5. A pillow for supporting the head of a user during sleeping according to claim 1, further comprising a cover generally enclosing the main body.

* * * * *